US007323488B2

(12) United States Patent
Burton

(10) Patent No.: US 7,323,488 B2
(45) Date of Patent: Jan. 29, 2008

(54) CHROMOGENIC ENZYME SUBSTRATES

(76) Inventor: Michael Burton, 14 Craven Court, Winwick Quay, Warrington, Cheshire WA2 8QU (GB)

( * ) Notice: Subject to any disclaimer, the term of this patent is extended or adjusted under 35 U.S.C. 154(b) by 468 days.

(21) Appl. No.: 10/493,483

(22) PCT Filed: Oct. 24, 2002

(86) PCT No.: PCT/GB02/04800

§ 371 (c)(1),
(2), (4) Date: Apr. 23, 2004

(87) PCT Pub. No.: WO03/035896

PCT Pub. Date: May 1, 2003

(65) Prior Publication Data

US 2005/0124556 A1 Jun. 9, 2005

(30) Foreign Application Priority Data

Oct. 24, 2001 (GB) ................................ 0125528.0
Sep. 18, 2002 (GB) ................................ 0221716.4

(51) Int. Cl.
*A61K 31/404* (2006.01)
*C07D 209/04* (2006.01)
*C07D 405/12* (2006.01)

(52) U.S. Cl. ...................... 514/414; 548/452; 548/465; 514/412; 514/415

(58) Field of Classification Search ................ 548/465, 548/452; 514/412, 414, 415
See application file for complete search history.

(56) References Cited

U.S. PATENT DOCUMENTS 5,364,767 A * 11/1994 Flowers et al. ............... 435/39
6,350,588 B1 * 2/2002 Roth et al. .................... 435/34

FOREIGN PATENT DOCUMENTS

FR 2 770 538 11/1997
WO WO 97/31008 8/1997

OTHER PUBLICATIONS

Berlin et al (1996): STN International HCAPLUS database, Columbus (OH), accession No. 1996: 734811.*
1. Masao Shiozaki, "Synthesis of 4',8-dihydroxyisoflavon-7-yl D-arabinofuranoside" Exploratory Chemistry Research Laboratories pp. 1477-1742 dated 1999.
2. Berlin et al. XP-002271582 In Situ Color Detection of L-Arabinofuranosidase, a "No-Background" Reporter Gene, with 5-Bromo-3-indolyl-a -L-arabinofuranoside pp. 171-174 (dated 1996).
3. XP-002214084 (abstract only).
4. XP-002214085 (abstract only).

* cited by examiner

*Primary Examiner*—Golam M. M. Shameem
(74) *Attorney, Agent, or Firm*—Whitham Curtis Christofferson & Cook, P.C.

(57) ABSTRACT

This invention provides novel chromogenic enzyme substrates which are indoxyl β-D-ribofuranosides. A process for their production is provided. Methods for detecting β-D-ribofuranosidase activity are given. The advantages of these novel compounds includes: detecting β-D-ribofuranosidase activity with high sensitivity and low substrate concentrations and use with other enzyme indicators in situations where a plurality of enzyme activities is to be visualized simultaneously e.g. for identifying bacteria growth on solid growth media. The synthesis and use of 5-bromo-4-chloro-3-indolyl-β-D-ribofuranoside is exemplified.

11 Claims, No Drawings

CHROMOGENIC ENZYME SUBSTRATES

This invention relates to chromogenic enzyme substrates.

Indicator enzyme substrates comprise an enzyme cleavable portion (eg a monosaccharyl) and a portion which forms a detectable indicator on cleavage (eg a chromogenic or fluorogenic group). A large number of glycoside-based enzyme substrates are known and are used extensively in microbiology, molecular biology and other fields. Glycosides of many different carbohydrates have been synthesised and utilised for detection purposes. The enzymes that are detected by these glycosides are often group specific (i.e. show relatively little specificity towards one portion of the substrate upon which they act) and therefore a wide variety of aglycones (i.e. indicator portions) can be tolerated. Thus, in the case of β-galactosidase many different β-galactosides have been used in the detection of it. Examples include o-nitrophenyl-, p-nitrophenyl-, indoxyls-(5-bromo-4-chloro-3-indolyl and 6-chloro-3-indolyl), 4-methylumbelliferyl-, 2-naphthyl-, 6-bromo-2-naphthyl-, cyclohexenoesculetin-(CHE), alizarin-, naphthol-ASBI- and phenyl-β-D-galactosides. Glycosides containing glucuronic acid, glucose, galactose, mannose, fucose, arabinose, N-acetylglucosamine, N-acetylgalactosamine, sialic acid, xylose, and cellobiose carbohydrate moieties are amongst those most frequently encountered in enzyme substrate applications. Many of these, such as β-D-glucuronides, α- and β-D-galactopyranosides and α- and β-D-glucopyranosides have found widespread use in the identification and enumeration of bacteria in areas such as clinical, food, veterinary, environmental and water microbiology. At the present time there are numerous commercial media and test kits available containing enzyme substrates, which show the presence of bacteria, yeast and other micro-organisms by the generation of coloured colonies or solutions.

Co-pending PCT application based on British Application 0125528.0 describes the synthesis of certain β-D-ribofuranoside derivatives as chromogenic substrates for the detection of β-D-ribofuranosidase activity through the generation of insoluble coloured precipitates that are formed from the aglycone portion after enzymatic cleavage. β-D-Ribofuranosidase activity is an enzyme activity capable of cleaving β-D-ribofuranosyl groups. GB 0125528.0 illustrates the utility of detecting β-D-ribofuranosidase activity in diagnostic microbiology. One feature of many of the exemplified molecules described in GB 0125528.0 is that the aglycones are derivatives of catechol. These substrates may be conveniently used in solid media such as agar-based media. By inclusion of an iron salt such as ferric ammonium citrate into the medium, these substrates produce brown or black insoluble precipitates that clearly indicate the site of enzymatic activity. This is useful in distinguishing microbes or other entities which possess β-D-ribofuranosidase activity from those which do not. A disadvantage of the very intense dark brown or black precipitate produced by substrates such as 3',4'-dihydroxyflavone-4'-β-D-ribofuranoside when used at diagnostically adequate concentrations is that it can mask the colour produced by another chromogenic substrate incorporated into the same medium for the detection of a different enzyme activity. It may readily be appreciated by those skilled in the art that under certain circumstances this is a disadvantage when trying to develop useful diagnostic media which depend on the visualisation of other enzyme activities in addition to, and simultaneously with, β-D-ribofuranosidase activity.

Indoxyl-glycosides of various monosaccharides have been reported and are readily available commercially. For example WO-A-99/50438 describes various indoxyl-glycosides including N-methyl-indoxyl-glycosides. Indoxyl-glycosides are well established as chromogenic enzyme substrates and they have found wide application in diagnostic microbiology including their use in solid media [M. Manafi, *Int. J. Food Microbiol.,* 31, 45, (1996)]. These substrates yield insoluble coloured precipitates after enzymatic cleavage. The coloured precipitate is derived mainly from two molecules of the cleaved aglycone, indoxyl, which combine via an oxidative process to form an indigo dye [S. Cotson and S. J. Holt, *Proc. Roy. Soc*. B, 148, 506, (1958)].

Although the precise observed colours of the insoluble precipitates may vary slightly depending on the exact conditions under which they are produced and may be influenced by, for instance, other components present in the media, the colour of the precipitate given by the principal indoxyl moieties commonly used in diagnostic microbiology may be described approximately as follows;

| Indoxyl | Colour |
|---|---|
| 5-Bromo-4-chloroindoxyl | Green |
| 5-Bromoindoxyl | Dark blue |
| Indoxyl | Blue |
| 5-Bromo-6-chloroindoxyl | Magenta |
| 6-Chloroindoxyl | Rose |

By choosing colours of these precipitates which are sufficiently contrasting, it is possible to design diagnostic media which detect two enzyme activities simultaneously by using two or more different indoxyl-substrates in which both the indoxyl and the carbohydrate or enzyme cleavable moieties are different in each substrate. Media of this nature have been described [J. N. Roth and W. J. Ferguson, U.S. Pat. No. 5,210,022 (1993); D. G. Flowers and M. Sternfeld, U.S. Pat. No. 5,364,767 (1994)]. One feature of interest with media containing different indoxyl substrates is that combinations of colours may be formed when two of the sought after enzyme activities are present in the same entity, and this can help to achieve a more selective detection system for the microbes under investigation.

The prior art contains several examples of the chemical synthesis of indoxyl-glycosides. All of these reported examples employ peracylated sugar halides as the glycosyl donor or, in the case of glucuronides, the equivalent methyl triacetylglucuronyl bromide [K. Yoshida et al., *Anal. Biochem.,* 58, 77, (1974); K. Yoshida et al, *Chem. Pharm. Bull.,* 32, 1759, (1975); A. N. Ley et al., *Can. J. Microbiol.,* 34, 690, (1988); S: Wolfe and R. J. Bowers, EP-A-0284725A2, (1988)]. The glycosyl acceptor is either a 1-acetylindoxyl derivative of the general formula (I) or, in one example, 3-acetyl-5-bromo-4-chloroindoxyl (1)

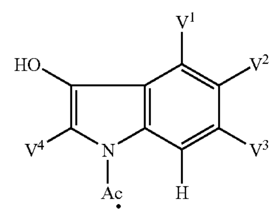

$V^{1-3}$ = H or Halogen, $V^4$ = H or $CO_2Me$

Most of these methods are base-promoted glycosylations and may therefore be considered as belonging to the classic Michael-type glycosylation (reaction in alcohol) or its variation as developed by Mannich (reaction in acetone/water). The first synthesis of an indoxyl-glycoside, indoxyl β-D-glucopyranoside (Plant Indican) was reported by Robertson in 1927 [A. Robertson, *J. Chem. Soc*, 1937, (1927)] using Mannich-type conditions. He succeeded in condensing 1-acetylindoxyl (I, V═H) with acetobromoglucose by use of potassium hydroxide in aqueous acetone to make the peracetylated indoxyl-glucoside intermediate. De-acetylation furnished the required indoxyl β-D-glucopyranoside. However, he preferred another route to the peracetylated intermediate, citing the then difficulty in preparing 1-acetylindoxyl as one reason for this. His alternative route involved condensing methyl indoxyl-2-carboxylate (I, $V^{1-3}$═H, $V^4$═$CO_2Me$) with acetobromoglucose, also by the aid of potassium hydroxide in aqueous acetone. However, several further steps were required before the desired final product could be obtained because of the need to de-carboxylate the indole nucleus at position-2, a process involving the forcing conditions of heating with sodium acetate in acetic anhydride at 160° C. The route involving the coupling of a protected sugar halide with the the appropriate methyl indoxyl-2-carboxylate has had little further application [A. Robertson and R. B. Waters, *J. Chem. Soc.*, 72, (1931); Ley et al., loc. cit; S. Wolfe and R. J. Bowers, loc. cit.]. The more expeditious route provided by the direct coupling of 1-acetylindoxyls with a fully acylated sugar halide (most often the acetobromosugar) has been the usual method of choice. This avoids the need for a de-carboxylation step. The necessary 1-acetylindoxyls (1, $V^4$═H) are very readily obtained by the methods developed by Holt and Sadler [S. J. Holt et al., *J. Chem. Soc.*, 1217, (1958); cf. S. J. Holt and P. W. Sadler, *Proc. Roy. Soc*. B, 148, 481, (1958)]. After coupling 1-acetylindoxyls with a peracylated sugar halide, Zemplén-type deprotection (sodium methoxide in methanol) yields the end product indoxyl glycoside. This approach was chosen by Anderson and Leaback [F. B. Anderson and D. Leaback, *Tetrahedron,* 12, 236, (1961)] for the synthesis of three 5-bromo-3-indolyl-based glycosides. In one example of theirs, 1-acetyl-5-bromoindoxyl (1, $V^2$═Br, $V^1$, $V^3$, $V^4$═H) was coupled with acetobromogalactose via the use of sodium hydroxide in aqueous acetone. After recovery of the peracetylated intermediate, the final product was obtained directly after de-protection with methanolic sodium methoxide and work-up. The synthesis of a 5-bromo-3-indolyl disaccharide from the acetobromosugar via the conditions of Anderson and Leaback has been reported recently [S. Kaneko et al., *Biosci. Biotechnol. Biochem.*, 64, 741, (2000)]. The range of halogenated indoxyl-monosaccharides was further extended by Horwitz and co-workers [J. P. Horwitz et al., *J. Med. Chem.*, 7, 574, (1964)]. In one synthesis by these investigators, 1-acetyl-5-bromo-4-chloroindoxyl (X—OH) (I, $V^1$═Cl, $V^2$═Br, $V^{3-4}$═H) was coupled with acetobromogalactose under the conditions used by Anderson and Leaback. After de-protection of the peracetylated indoxyl-galactoside they obtained 5-bromo-4-chloro-3-indolyl β-D-galactopyranoside (X-Gal). X-Gal is currently the most widely encountered indoxyl-glycoside used in diagnostic microbiology as well as in other fields such as molecular biology. In the same paper, Horwitz and co-workers also employed 3-acetyl-5-bromo-4-chloroindoxyl [S. J. Holt and P. W. Sadler, ioc. cit.] as an intermediate. Using this reactant it was necessary to remove the 3-acetyl group with sodium in methanol to generate the indoxyl sodium salt in situ prior to treating it with acetobromoglucose. Because the conditions of the reaction also led to the removal of all the other acetyl protecting groups, the fully deprotected glycoside, 5-bromo-4-chloro-3-indolyl β-D-glucopyranoside (X-glucoside) was furnished in a single step. However this route has three distinct disadvantages. Firstly, 3-acetylindoxyls are more difficult to prepare than 1-acetylindoxyls. Secondly, their much reduced stability makes them more difficult to work with. Thirdly, because the reaction is "one-pot" and the yield is low, there is a substantial quantity of highly coloured residue which has to be removed before the product can be usefully employed as an enzyme substrate, and this is very cumbersome to accomplish satisfactorily on a large preparative scale.

More recently, Berlin and Sauer [W. Berlin and B. Sauer, *Anal. Biochem.*, 243, 171, (1996)] reported difficulty with the base promoted reaction between 1-acetyl-5-bromoindoxyl (I, $V^2$═Br, $V^1$, $V^3$, $V^4$═H) and a perbenzoyl-arabinofuranosyl bromide. However, they were able to obtain a successful glycosylation reaction by using silver triflate as the catalyst in dichloromethane. These conditions represent a variation of the classic Koenigs-Knorr reaction [K. Toshima and K. Tatsuta, *Chem. Rev.*, 93, 1503, (1993)].

Before the present invention, indoxyl derivatives of β-D-ribofuranosides had not been described.

A first aspect of this invention provides an indoxyl β-D-ribofuranoside, of the formula II

II

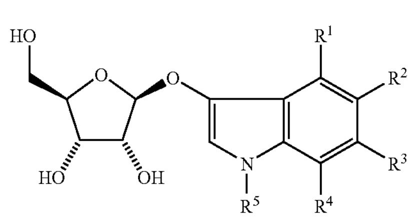

wherein $R^{1-4}$ are independently H, halide, nitro or $C_{1-6}$alkyl groups and $R^5$ is H, $C_{1-6}$alkyl, or aralkyl or a substituted derivative or ester of the indoxyl β-D-ribofuranoside.

A second aspect of this invention provides a process for producing an indoxyl β-D-ribofuranoside according to the first aspect of this invention; comprising a) contacting a protected β-D-ribofuranosyltrichloroacetimidate with a compound of formula III

III

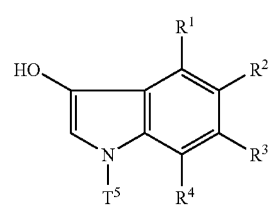

wherein $R^{1-4}$ are independently H, halide, nitro or $C_{1-6}$alkyl groups and $T^5$ is, acyl, trialkylsilyl or other protecting groups in the presence of a catalyst to form a protected indoxyl-β-D-ribofuranoside; and b) removing the protecting groups.

Protecting groups are moieties attached to reactive hydroxyl groups on β-D-ribofuranosyl or the indoxyl nitrogen to prevent reactions occurring which are not required. The most commonly used protecting group is acetyl.

A third aspect of this invention provides a method for detecting β-D-ribofuranosidase activity in a sample comprising;

a) contacting the sample with an indoxyl β-D-ribofuranoside according to the first aspect of this invention; wherein said indoxyl β-D-ribofuranoside comprises a β-D-ribofuranosyl moiety and an indoxyl moiety, said β-D-ribofuranosyl moiety being cleavable by β-D-ribofuranosidase from the indoxyl moiety releasing the indoxyl moiety which forms a coloured compound; and b) concluding whether β-D-ribofuranosidase activity is present by detecting whether a coloured compound is formed from the indoxyl moiety.

According to a fourth aspect of this invention a kit is provided comprising a) an indoxyl β-D-ribofuranoside according to the first aspect of this invention and b) a component for use in producing a microbial growth medium.

According to a fifth aspect of this invention a composition is provided which comprises an indoxyl β-D-ribofuranoside according to the first aspect of this invention and another component.

Upon cleavage by β-D-ribofuranosidase, the indoxyl moiety of indoxyl β-D-ribofuranosides would produce a range of coloured compounds, as indicated above different from those given by the catechol-derived β-D-ribofuranosides exemplified in GB 0125528.0. Furthermore, unlike compounds such as those formed from 3',4'-dihydroxyflavone-4'-β-D-ribofuranoside in a medium containing an iron salt, the coloured compound produced by indoxyl β-D-ribofuranosides after enzymatic cleavage is not likely to mask completely the colour generated by a different enzyme substrate, (such as the coloured compound produced by a different indoxyl portion attached to another sugar or enzyme cleavable group), incorporated into the medium for the visualisation of a different enzyme activity. Moreover, it is envisaged that some new chromogenic media of the present invention would enable the presence of β-D-ribofuranosidase activity to be detected by the use of a chromogenic β-D-ribofuranoside which is masked by a second, more highly coloured compound liberated by a different enzyme activity in the same sample after its action upon a second chromogenic enzyme substrate. It will be appreciated by those skilled in the art that under certain circumstances this represents an advantage when trying to develop useful diagnostic media which depend on the visualisation of other enzyme activities in addition to β-D-ribofuranosidase activity. It was therefore considered that the synthesis of indoxyl β-D-ribofuranosides and their application as chromogenic enzyme substrates is complementary to that of the catechol-based β-D-ribofuranosides exemplified in GB 0125528.0 and therefore overcomes the present limitations in designing novel chromogenic media in which the detection of β-D-ribofuranosidase activity is critical.

Indoxyl β-D-ribofuranosides of the current invention are defined by formula II above. It is generally preferred that positions $R^1$ to $R^4$ are H, $C_{1-6}$ alkyl or halide and the halides are generally bromo or chloro. $R^5$ can be $C_{1-6}$ alkyl or aralkyl such as benzyl, but is generally H or methyl. Specially preferred indoxyl portions are selected from the group consisting of 5-bromo-4-chloro-3-indolyl (also called X), 5-bromo-6-chloro-3-indolyl, 5-bromo-3-indolyl, 6-chloro-3-indolyl, 3-indolyl, 4-chloro-3-indolyl, 6-bromo-3-indolyl, 6-fluoro-3-indolyl, 5,7-dibromo-3-indolyl, 4,5-dichloro-3-indolyl, 5-nitro-3-indolyl, 1-methyl-3-indolyl, 5-bromo-4-chloro-1-methyl-3-indolyl, 5-bromo-6-chloro-1-methyl-3-indolyl, 5-bromo-1-methyl-3-indolyl, 6-chloro-1-methyl-3-indolyl, 4-chloro-1-methyl-3-indolyl, 6-bromo-1-methyl-3-indolyl, 6-fluoro-1-methyl-3-indolyl, 5,7-dibromo-1-methyl-3-indolyl, 5,6-dibromo-3-indolyl, 5,6-dibromo-1-methyl-3-indolyl and 5-nitro-1-methyl-3-indolyl and 4,5-dichloro-1-methyl-3-indolyl.

The second aspect of this invention provides a process for producing indoxyl β-D-ribofuranosides and was developed after protracted and in-depth studies carried out by the inventor.

In order to provide compounds of the invention, it was attempted first to try coupling 1-acetyl-5-bromo4-chloroindoxyl (X—OH) (1-acetyl-5-bromo4-chloroindol-3-ol) with acetobromo- or acetochlororibofuranose under the conditions used by Andersen and Leaback (loc. cit.) to make 5-bromo-3-indolyl glycosides and by Horwitz and co-workers (loc. cit.) to make X-Gal, the target molecule of the present invention therefore being 5-bromo-4-chloro-3-indolyl β-D-ribofuranoside (X-β-D-ribofuranoside). Thus, either acetobromoribofuranose or the somewhat more stable acetochlororibofuranose [H. Zinner, *Chem. Ber.,* 83, 153, (1950)] (both prepared from commercially available β-D-ribofuranose tetraacetate) and X—OH were treated with the appropriate quantity of sodium or potassium hydroxide in aqueous acetone. Analysis of the reactions by tic (for the appearance of a new UV active product) and, where appropriate, by isolating any new products formed by column chromatography on silica gel C60 followed by nmr analysis, showed that none of the reactions produced the expected protected indoxyl-ribofuranoside intermediate.

Ribosylation was then tried using the tribenzoyl-D-ribofuranosyl bromide [S. Hanessian and A. G. Pernet, *Can. J. Chem.,* 52, 1280, (1974)] and chloride [H. M. Kissman et al., *J. Amer. Chem. Soc.,* 77, 18, (1955)]. Nonetheless, no product formation was observed in these reactions also. Owing to the failure to couple X—OH to a peracylated ribofuranosyl halide under the influence of either potassium or sodium hydroxide, an alternative glycosylation procedure employing these halides was sought The Koenigs-Knorr reaction using protected sugar halides is a widely used procedure to construct Olycosides and has already been applied in the indoxyl-series [W. Berlin and B. Sauer, loc. cit.]. Originally developed using silver salts as both the catalyst and the halide acceptor [W. Koenigs and E. Knorr, *Chem. Ber.,* 34, 957, (1901)], the scope of the reaction has been extended over the years by the use of other metal catalysts [K. Toshima and K. Tatsuta, loc. cit.]. Several of these were explored during work on the present invention with the aforementioned peracetyl- and perbenzoylribofuranosyl halides. Using the solvents, acetonitrile, chloroform, dichloromethane, diethyl ether, dimethylformamide, nitromethane or pyridine, the following glycosylation catalysts were tried, all without success; silver(I)carbonate, silver(I)cyanide, silver(I)oxide, silver(I)nitrate, silver(I)triflate, cadmium carbonate, mercury(II)bromide, mercury(II) chloride, and mercury(II)oxide.

The failure of the Koenigs-Knorr reaction to produce the desired glycoside led to the assessment of other glycosylation methods not entailing the intermediary of a glycosyl halide in the key coupling step. The use of 1-O-acylated glycosyl donors in glycosylations (Helferich reaction) was first demonstrated in 1933 [B. Helferich and E. Schmitz-Hillebrecht, *Chem. Ber.,* 66, 378, (1933)]. This reaction often involves heating a peracylated sugar with an aglycone in the presence of a Lewis acid promoter such as p-toluenesulfonic acid (PTSA), or zinc chloride [E. M. Montgomery, N. K. Richtmyer and C. S. Hudson, *J. Amer. Chem. Soc.,* 64, 690, (1942)]. Heating β-D-ribofuranose tetraacetate and X—OH with either of these promoters failed to give the desired product. Since the initial experiments of Helferich and co-workers, the scope of the Helferich reaction has been further extended by the use of other catalysts and by conducting the reaction in organic solvents. Indeed, ribofuranosylation of aromatic compounds has been reported using peracylated, β-D-ribofuranoses in organic solvents with boron trifluoride diethyl etherate as the catalyst [L. Kalvoda, *Coll. Czech. Chem. Comm.,* 38, 1679, (1973) and the PCT application based on 0125528.0]. However, substitution of X—OH for the aromatic compounds used in these examples gave no riboside. Additional Helferich reactions were attempted in acetonitrile, chloroform, dichloromethane, 1,2-dichloroethane, diethyl ether, and nitromethane with either β-D-ribofuranose tetraacetate, 1-O-acetyl-β-D-ribofuranose tribenzoate or 1-p-nitrobenzoyl-β-D-ribofuranose tribenzoate and the following Lewis acid catalysts; aluminium trichloride, boron trifluoride diethyl etherate, iron(III)chloride, tin(IV)chloride, TMS-triflate and PTSA. No reaction was successful.

Thioglycosides have proved versatile as glycosyl donors [K. Toshima and K. Tatsuta, loc. cit. ]. A reagent considered suitable for ribosylation, phenylthio β-D-ribofuranoside, was conveniently prepared from β-D-ribofuranose tetraacetate and thiophenol [G. Kim et al., *Tetr. Lettr.* 34, 7627, (1993)]. Treatment of this thioglycoside and X—OH with either mercury(II)chloride or mercury(II)sulfate as the promoter in dichloromethane or nitromethane failed to induce any riboside formation. Crich and Smith have recently developed a glycosylation procedure based on thioglycosides that is both mild and has been applied to a range of aglycones [D. Crich and M. Smith, *J. Amer. Chem. Soc.,* 123, 9015, (2001)]. The Crich glycosylation involves treating the appropriate thioglycoside and glycosyl acceptor with 1-benzenesulfinyl piperidine (BSP) and trifluoromethanesulfonic anhydride ($Tf_2O$) in dichloromethane at low temperature (−60° C.), either with or without the hindered base 2,4,6-tri-tert-butylpyrimidine (TTBP). When these conditions were applied to phenylthio β-D-ribofuranoside and XOH, no reaction was observed, neither with nor without the presence of TTBP.

Yet another access to glycosides not involving a 1-halide intermediate in the key glycosylation stage is the trichloroacetimidate method of Schmidt [R. R. Schmidt, *Angew. Chem. Int. Ed. Engl.,* 25, 212 (1986)]. Ribofuranosyl trichloroacetimidates have been utilised as ribofuranosyl donors in glycosides syntheses [I. Chiu Machado et al., *J. Carbohydr. Chem.,* 13, 465, (1994)]. The most suitable donor for coupling with X—OH would be a peracylated ribofuranosyl trichloroacetimidate. This is because all the acyl groups on the protected-coupled product could be conveniently removed in one step by the Zemplén procedure as described for other indoxyl-glycosides. The synthesis of two peracylated ribofuranosyl trichloroacetimidates has been described by Verez-Bencomo and co-workers [I. Chiu-Machado et al., *J. Carbohydr. Chem.,* 14, 551, (1995)]. Peracetylated D-ribofuranosyl trichloroacetimidate, obtained as an anomeric mixture, was successfully used by them to produce β-D-ribofuranosides, although they did not report its use with aromatic aglycones. The starting point of their synthesis of this ribosyl donor was methyl 2,3,5-tri-O-acetyl-β-D-ribofuranoside. This is prepared by acetylation of methyl β-D-ribofuranoside with acetic anhydride [S. J. Angyal et al., *Carbohdyr. Res.,* 157, 83, (1986)]. Methyl β-D-ribofuranoside is itself prepared conveniently from ribose [R. Barker and H. G. Fletcher Jr, *J. Org. Chem.,* 26, 4605, (1961)]. Reaction of the peracetylated D-ribofuranosyl trichloroacetimidate with XOH in dichloromethane at ambient temperature using TMS-triflate as the catalyst afforded new material which was UV active on tic. Separation of this material from other compounds by column chromatography on silica gel C60 followed by work-up resulted in the isolation of the requisite X-β-D-ribofuranoside peracetate essentially free from any significant impurities. De-acetylation with a catalytic quantity of sodium methoxide in methanol, followed by evaporation of the solvent and trituration of the solid gave X-β-D-ribofuranoside as a solid with a purity by HPLC of around 96%. [HPLC conditions: Column; Chromosphere 250 mm×4.6 mm $C_{18}$ reverse-phase silica gel 5μ (ChromosExpress, Macclesfield, UK); solvent; methanol/water 1:1 v/v, 1 ml/min flow; detection, UV at 290 nm; loading, 1 mg of product in 1 g of solvent, 20 μl injection; run time, 30 min; retention time approximately 17 minutes].

The process described in the second aspect of this invention is generally carried out with step a) occurring in an organic solvent.

The process of this invention is generally carried out with the catalyst of step a) being a Lewis acid.

It is preferred that the process of this invention is carried out with the protected β-D-ribofuranosyl trichloroacetimidate being selected from the group consisting of 2,3,5-tri-O-acetyl-β-D-riboturanosyl trichloroacetimidate and 2,3,5-tri-O-benzoyl-β-D-ribofuranosyl trichloroacetimidate.

As described above $T^5$ in formula III can be acyl, a trialkylsilyl protecting group or other protecting group. The most useful trialkylsilyl protecting groups are trimethylsilyl, t-butyidimethylsilyl, triethylsilyl and triisopropylsilyl. The preferred protecting group at $T^5$ is acetyl or trimethylsilyl. When the protecting groups are removed during step b) $T^5$ may be converted into $R^5$. This may be the procedure followed when $T^5$ is acetyl and $R^5$ is H. Alternatively no change may occur and $T^5$ and $R^5$ are identical. In another embodiment $T^5$ may be modified in a separate step to produce $R^5$. For example, after step a) the intermediate product may have an acetyl group at $T^5$ which is selectively deacetylated and a subsequent reaction at the indoxyl-N produces $R^5$. A further deprotection occurs, step b), before the indoxyl β-D-ribofuranoside is produced.

As described above, the third aspect of this invention provides a method for detecting β-D-ribofuranosidase activity in a sample.

In this aspect of the invention there may also be a preliminary step in which the sample which contains cells, usually microbial cells, is grown in or on a medium.

In an alternative embodiment the method may also comprise detecting a second enzyme activity in the sample and in step a) the sample is additionally contacted with a second enzyme substrate comprising an enzyme cleavable moiety which is not β-D-ribofuranosyl and an indicator moiety which is not identical to that of the indoxyl β-D-ribofuranoside, said enzyme cleavable moiety being cleavable by the second enzyme activity releasing the indicator moiety which forms a second detectable compound; and c) concluding whether the second enzyme activity is present in the sample by detecting whether. a second detectable compound is formed from the indicator moiety of the second enzyme substrate.

The second enzyme substrate comprises an indicator moiety which is generally a chromogenic moiety, but can also be a fluorogenic moiety. It is preferred that the second enzyme substrate comprises an enzyme cleavable moiety which is a sugar moiety or a phosphate or an ester such as a caprylate.

In the method of the third aspect of this invention the sample may comprise living cells such as bacteria or other prokaryotes, fungi, eukaryotic organisms, cell cultures or alternatively cell extracts.

It is preferred that the detection methods of this invention occur with the sample on a solid medium and the coloured compound or compounds produced are insoluble.

In a specially preferred embodiment of this invention the method of the third aspect of this invention comprises a solid medium comprising an indoxyl β-D-ribofuranoside of the current invention.

In one embodiment of the method the coloured compound formed from the indoxyl portion of the indoxyl-β-D-ribofuranoside is visualised simultaneously with a coloured compound formed from a chromogenic moiety of the second enzyme substrate.

In an alternative embodiment a coloured compound formed from the chromogenic moiety of the second enzyme substrate masks the coloured compound formed from the indoxyl moiety of the indoxyl β-D-ribofuranoside substrate.

In an alternative embodiment of the third aspect of this invention the sample is in a liquid microbial growth medium.

The fourth aspect of this invention, as described above, provides a kit for carrying out detection using an indoxyl β-D-ribofuranoside of the current invention. It is preferred that the component for use in producing a medium is for producing a solid microbial growth medium.

According to a fifth aspect of the invention, as described above, the other component in the composition is a component of solid media. Alternatively the other component may be another chromogenic enzyme substrate. A composition of this invention may comprise a plurality of other components sufficient to form a detection medium useful in this invention.

The current invention is further illustrated by the following examples.

EXAMPLE 1

Synthesis of 5-bromo-4-chloro-3-indolyl β-D-ribofuranoside (X-β-D-ribofuranoside)

The reaction was conducted in a 500 ml two-necked flask equipped with a magnetic stirrer.

To a mixture of 2,3,5-tri-O-acetyl-α/β-D-ribofuranosyl trichloroacetimide [I. Chiu-Machado et al., (1995), loc. cit.] (145.0 g) and 3 Å molecular sieves (2.0 g) in dry dichloromethane (300 ml) was added dry X—OH (82.9 g) and the whole mixture was stirred at room temperature for 10 mins. TMS-triflate (8 ml) was then added in one portion by syringe and the reaction was left stirring at room temperature for 1 hour. The mixture was then poured into dichloromethane (3 L) and washed with 1 M sodium hydroxide (4×2 L). The organic layer was separated, filtered through celite and concentrated, in vacuo, to low volume (approx. 1 L). The organic layer was then further washed with 1 M sodium hydroxide (6×1 L) and deionised water (1 L) After drying (magnesium sulfate) it was filtered through celite and concentrated, in vacuo, to afford the crude protected product as a dark brown solid (87.4 g).

The dark brown solid was examined by tic and found to contain two main products with $R_f$ values of approximately 0.37 (the protected β-ribofuranoside) and 0.43. [Silica gel plates, 60/80 petroleum ether, ethyl acetate 1:1 v/v, uv at 254 nm]. Flash chromatography of the crude product on Silica Gel C60 (600 g) using 60/80 petroleum ether/ethyl acetate/triethylamine 1:1:0.05 v/v/v as the eluting solvent gave the protected product as a brown oil (55 g). The oil was mainly a mixture of the X-β-D-ribofuranoside tetraacetate and the contaminant with $R_f$ 0.43. This oil was taken up in warm methanol (30 ml) and after leaving at ambient temperature a precipitate was formed. After 16 hours, the cream coloured solid consisting almost entirely of material with $R_f$ value 0.43 was removed by filtration, and the filtrate concentrated at 40° C. in vacuo to afford X-β-D-ribofuranoside tetraacetate as a brown oil (33.6 g).

X-β-D-ribofuranoside tetraacetate (30 g) was dissolved in methanol (200 ml) and 5 ml of a solution of sodium methoxide (made from 1 g sodium in 20 ml of methanol) was added dropwise until the solution reached pH10. The solution was left standing at room temperature for 90 mins. then concentrated, in vacuo, to a brown tarry oil. The oil was triturated in acetone (500 ml). A grey solid-precipitated and this was removed by vacuum filtration. The solid was discarded and the filtrate was concentrated in vacuo, to a brown oil (19.3 g). The oil was triturated with methanol (80 ml) and the product precipitated as a pale blue solid which was recovered by filtration (2.57 g). The filtrate was concentrated, in vacuo, and triturated with methanol (30 ml) to obtain a second crop as a pale cream solid that was also recovered by filtration (4.04 g). Both crops were combined and washed with cold acetone (approx. 20 ml) followed by filtration to recover the title compound as a white solid (approx. 2.5 g).

EXAMPLE 2

Comparison of the Attributes of Substrates for β-D-ribofuranosidase

The following media were produced to demonstrate the utility of the compounds of the current invention.

| Medium A (components per liter) | |
|---|---|
| Columbia agar (Oxoid) | 40 g |
| 5-Bromo-4-chloro-3-indolyl β-D-ribofuranoside (also known as X-β-D-ribofuranoside, a compound of this invention) | 80 mg |
| 6-chloro-3-indolyl β-D-glucopyranoside | 200 mg |
| **Medium B (components per liter)** | |
| Columbia agar (Oxoid) | 40 g |
| 3'4'-dihydroxyflavone-4'-β-D-ribofuranoside | 300 mg |
| 6-chloro-3-indolyl β-D-glucopyranoside | 200 mg |
| Ferric ammonium citrate | 500 mg |
| **Medium C (components per liter)** | |
| Columbia agar (Oxoid) | 40 g |
| 5-Bromo-4-chloro-3-indolyl β-D-ribofuranoside (X-β-D-ribofuranoside) | 80 mg |
| 3,4-cyclohexenoesculetin-β-D-galactopyranoside | 300 mg |
| Isopropyl-β-D-thiogalactopyranoside | 30 mg |
| Ferric ammonium citrate | 500 mg |
| **Medium D (components per liter)** | |
| Columbia agar (Oxoid) | 40 g |
| 5-Bromo-4-chloro-3-indolyl β-D-ribofuranoside (X-β-D-ribofuranoside) | 80 mg |
| 3'4'-dihydroxy-3-methoxyflavone-4'-β-D-galactopyranoside | 300 mg |
| Isopropyl-β-D-thiogalactopyranoside | 30 mg |
| Ferric ammonium citrate | 500 mg |

-continued

| Medium E (components per liter) | |
|---|---|
| Columbia agar (Oxoid) | 40 g |
| 5-Bromo-4-chloro-3-indolyl β-D-ribofuranoside (X-β-D-ribofuranoside) | 80 mg |
| Medium F (components per liter) | |
| Columbia agar (Oxoid) | 40 g |
| 3'4'-dihydroxyflavone-4'-β-D-ribofuranoside | 300 mg |
| Ferric ammonium citrate | 500 mg |

The flavone derivatives used in Media B, D and F are synthesised as described in copending PCT application claiming priority from GB 0125532.2.

All components were added to 1 litre of deionised water and autoclaved at 116° C. for 10 minutes. Culture plates were prepared from molten agar at 50° C. and dried. Various control strains with known enzymatic characteristics were prepared at a suspension of approximately $10^8$ cfu/ml using a densitometer 10 μl of this suspension was inoculated onto each of the different types of media and incubated overnight at 37° C. The cultural appearance of the various strains tested are shown in Table 1.

TABLE 1

Colonial appearance of various strains on various chromogenic agars.

| | A | B | C | D | E | F |
|---|---|---|---|---|---|---|
| *Enterobacter cloacae* NCTC 11936 | Purple | Black | Black | Black | Green | Black |
| *Escherichia coli* NCTC 10418 | Green | Black | Black | Black | Green | Black |
| *Klebsiella pneumoniae* NCTC 10896 | Purple | Black | Black | Black | Green | Black |
| *Salmonella typhimurium* NCTC 74 | Green | Black | Green | Green | Green | Black |
| *Serratia marcescens* NCTC 10211 | Purple | Black | Green | Black | Green | Black |
| *Yersinia enterocolitica* NCTC 11176 | Colourless | Colourless | Colourless | Grey/black | Colourless | Colourless |

| | E |
|---|---|
| *Acinetobacter lwoffii* ATCC 15309 | Colourless |
| *Aeromonas hydrophila* NCTC 8049 | Green |
| *Citrobacter freundii* NCTC 9750 | Green |
| *Enterobacter aerogenes* NCIMB 10102 | Green |
| *Escherichia coli* 0157 NCTC 12079 | Green |
| *Shigella boydii* NCTC 9327 | Green |
| *Vibrio cholerae* NCTC 12945 | Colourless |
| *Pseudomonas aeruginosa* NCTC 10662 | Colourless |

The above described analysis indicates that when X-β-D-ribofuranoside (5-bromo-4-chloro-3-indolyl β-D-ribofuranoside) was tested with Rose glucoside (6-chloro-3-indolyl β-D-glucopyranoside) strains which produced both β-D-ribofuranosidase and β-glucosidase produced a mixture of colors due to hydrolysis of both chromogenic substrates (see results for medium A). Such colonies were clearly distinguishable from those which hydrolysed only one or neither of the two substrates.

This attribute of X-β-D-ribofuranoside is not shown by 3'4'-dihydroxyflavone-4'-β-D-ribofuranoside as the iron chalet of 3',4'-dihydroxyflavone masked the presence of any β-glucosidase activity (see results for medium B). Just as this glucosidase reaction may be masked, the hydrolysis of X-β-D-ribofuranoside itself may be masked by other chelating chromogens. For example, the results from media C and D show that the hydrolysis of X-β-D-ribofuranoside may be masked when either 3,4-cyclohexenoesculetin-β-D-galactopyranoside or 3'4'-dihydroxy-3-methoxyflavone-4'-β-D-galactopyranoside are present in the medium.

The results demonstrated above for X-β-D-ribofuranoside demonstrate the three advantages of the current invention. Firstly the indoxyl β-D-ribofuranosides of this invention have the ability to detect β-D-ribofuranosidase activity with high sensitivity and low substrate concentrations. Secondly, the indoxyl β-D-ribofuranosides of this invention can be used simultaneously with other indoxyl substrates to produce a medium on which a plurality of colours may be generated.

Thirdly the indoxyl β-D-ribofuranosides of this invention may also be used simultaneously with chelation based substrates which produce an indicator capable of masking the coloured precipitate generated from the indoxyl portions following β-D-ribofuranosidase activity.

The invention claimed is:

1. An indoxyl β-D-ribofuranoside of the Formula II

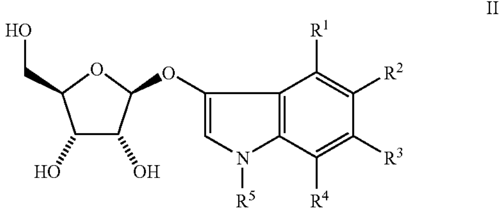

II wherein $R^{1-4}$ are independently selected from the group consisting of H, halide, nitro and $C_{1-6}$ alkyl; and $R^5$ is selected from the group consisting of H, $C_{1-6}$ alkyl and aralkyl;

or a substituted derivative of the indoxyl β-D-ribofuranoside.

2. An indoxyl compound according to claim 1 wherein the group

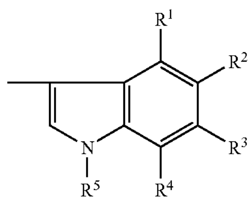

is selected from the group consisting of 5-bromo-4-chloro-3-indolyl, 5-bromo-6-chloro-3-indolyl, 5-bromo-3-indolyl, 6-chloro-3-indolyl, 3-indolyl, 4-chloro-3-indolyl, 6-bromo-3-indolyl, 6-fluoro-3-indolyl, 5,7-dibromo-3-indolyl, 4,5-dichloro-3-indolyl, 5-nitro-3-indolyl, 1-methyl-3-indolyl, 5-bromo-4-chloro-1-methyl-3-indolyl, 5-bromo-6-chloro-1-methyl-3-indolyl, 5-bromo-1-methyl-3-indolyl, 6-chloro-1-methyl-3-indolyl, 4-chloro-1-methyl-3-indolyl, 6-bromo-1-methyl-3-indolyl, 6-fluoro-1-methyl-3-indolyl, 5,7-dibromo-1-methyl-3-indolyl, 5,6-dibromo-3-indolyl, 5,6-dibromo-1-methyl-3-indolyl and 5-nitro-1-methyl-3-indolyl and 4,5-dichloro-1-methyl-3-indolyl.

3. An indoxyl compound according to claim 2 wherein said group is 5-bromo-4-chloro-3-indolyl.

4. A process for producing an indoxyl β-D-ribofuranoside according to claim 1 comprising;

a) contacting a protected-β-D-ribofuranosyl trichloroacetimidate with a compound of formula (III)

III

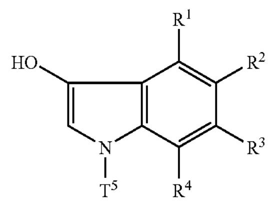

wherein $R^{1-4}$ are independently selected from the group consisting of H, halide, nitro and $C_{1-6}$ alkyl and $T^5$ is selected from the group consisting of acyl, trialkylsilyl and other protecting groups in the presence of a catalyst to form a protected indoxyl-β-D-ribofuranoside; and b) removing the protecting groups.

5. A process according to claim 4 wherein $T^5$ is an acetyl or a trimethylsilyl group.

6. A process according to claim 4 which additionally comprises intermediate steps between step a) and step b) to convert $T^5$ to $R^5$.

7. A process according to claim 4 wherein the protected β-D-ribofuranosyl trichloroacetimidate is selected from the group consisting of 2,3,5-tri-O-acetyl-β-D-ribofuranosyl trichloroacetimidate and 2,3,5-tri-O-benzoyl-β-D-ribofuranosyl trichloroacetimidate.

8. A composition comprising an indoxyl β-D-ribofuranoside according to claim 1 and another component.

9. A composition according to claim 8 wherein the other component is a component of a solid microbial medium.

10. A composition according to claim 8 wherein the other component is another enzyme substrate.

11. A composition according to claim 10 in which the second enzyme substrate is selected from 6-chloro-3-indolyl β-D-glucopyranoside, 3,4-cyclohexeno esculetin-β-D-galactopyranoside, and 3',4'-dihydroxy-3-methoxy flavone-4'-β-D-galacto pyranoside.

* * * * *